United States Patent [19]
Portney

[11] Patent Number: 6,152,959
[45] Date of Patent: Nov. 28, 2000

[54] IRIS FIXATED INTRAOCULAR LENS

[76] Inventor: Valdemar Portney, 11940 N. Riviera, Tustin, Calif. 92782

[21] Appl. No.: 09/312,566

[22] Filed: May 14, 1999

[51] Int. Cl.$^7$ ........................................................ A61F 2/16
[52] U.S. Cl. ........................ 623/6.51; 623/6.38; 623/6.4; 623/6.41; 623/6.42; 623/6.43
[58] Field of Search .................................... 623/6.38, 6.4, 623/6.41, 6.42, 6.43, 6.47, 6.51

[56] References Cited

U.S. PATENT DOCUMENTS

| | | |
|---|---|---|
| Re. 32,525 | 10/1987 | Pannu . |
| B1 Re. 32,525 | 5/1989 | Pannu . |
| 4,215,440 | 8/1980 | Worst . |
| 4,435,855 | 3/1984 | Pannu . |
| 4,542,540 | 9/1985 | White . |
| 4,542,541 | 9/1985 | Pannu . |
| 5,192,319 | 3/1993 | Worst . |

OTHER PUBLICATIONS

Artisan™ Phakic Intraocular Lenses "Focus on Perfection" Ophtec Laboratories (7 Sheets).

Primary Examiner—Dinh X. Nguyen
Attorney, Agent, or Firm—Howard R. Lambert

[57] ABSTRACT

An iris fixated intraocular lens for implanting in the anterior chamber of an eye comprises an optic having an optical axis and anterior and posterior sides; and first and second fixation members, each of the fixation members having a proximal end region and a distal end region. The proximal end region of each fixation member is a single flexible strand fixed to an edge region of the optic to extend generally tangentially outwardly therefrom and the distal end region is formed into a loop having defined therein at least one narrow iris pincher gap for detachably attaching the intraocular lens to the anterior surface of the iris. The first and second fixation members are substantially identical to one another and are attached to the optic on opposite sides of the optical axis. The optic is preferably constructed from an elastically deformable plastic material, such as silicone or an acrylic, so that the resulting three-piece intraocular lens can be folded or otherwise deformed for implanting into an eye through a small, preferably sutureless, surgical incision. Variation IOLs are disclosed, such variations relating to iris pincer gaps.

29 Claims, 4 Drawing Sheets

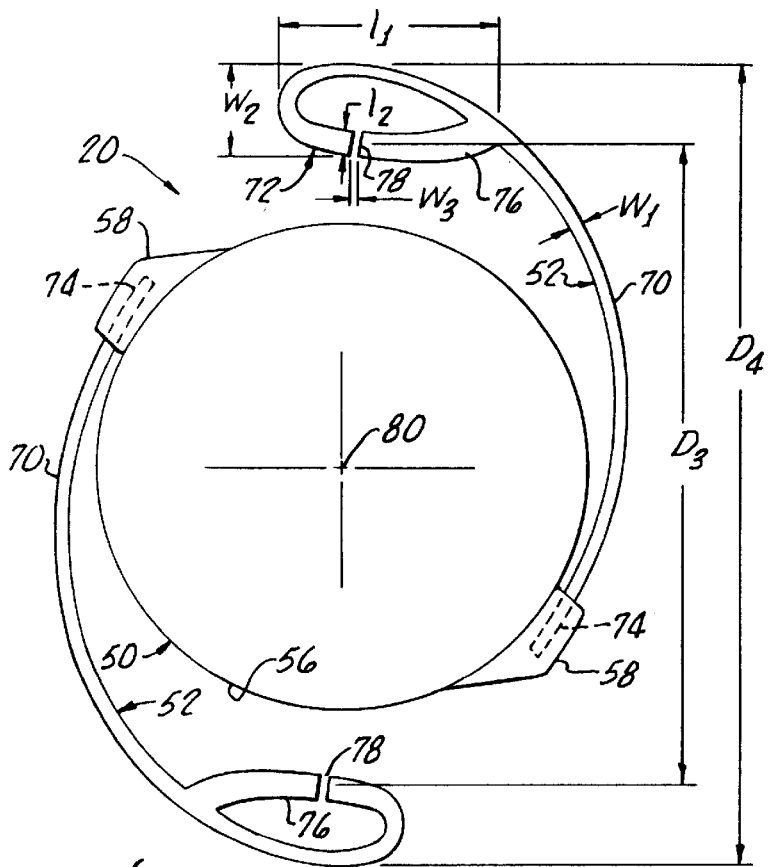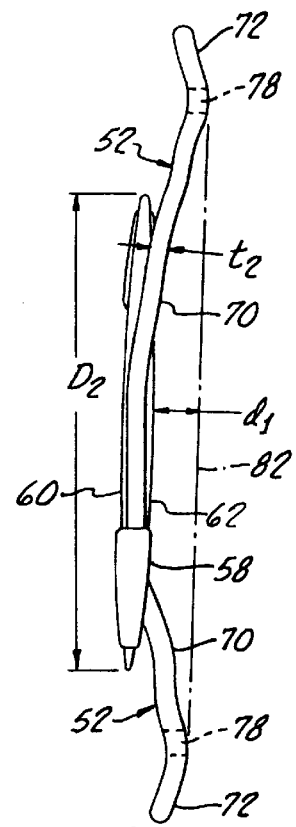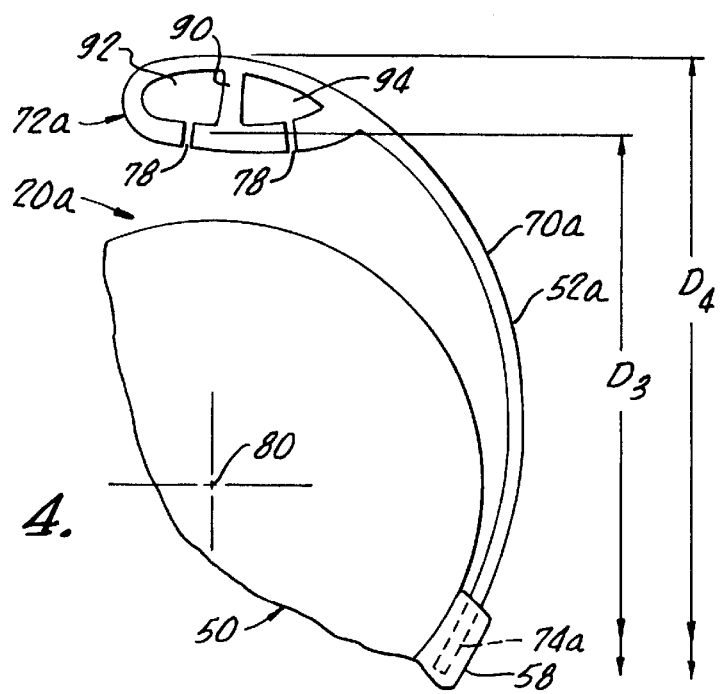
Fig. 2.
Fig. 3.
Fig. 4.

IRIS FIXATED INTRAOCULAR LENS

BACKGROUND OF THE INVENTION

1. Field of the Invention

The present invention relates generally to the field of ophthalmics, more particularly to ophthalmic devices, and still more particularly to ophthalmic devices known as intraocular lenses (IOLs).

2. Background Discussion

At the onset it may be helpful to the understanding of the present invention to define the term "phakic" as it relates to human eyes. The term "phakic" is applied to an eye in which the natural ocular lens is still present. This is in contrast to an aphakic eye from which the natural ocular lens has—for any reason—been removed. A phakic eye is considered a dynamic or active eye because the living natural lens is subject to change over time, while an aphakic eye is considered a static eye because the natural lens has been removed.

Vision in an eye is enabled by light from a viewed image being-refracted to the retina by the cornea and the natural lens (and/or any implanted intraocular lens) located posterior of the cornea.

One relatively common ocular problem is impaired or complete loss of vision due to the natural ocular lens becoming cloudy or opaque—a condition known as cataract. The formation of cataracts is typically associated with natural bodily aging, and most individuals over the age of about 60 years suffer from cataracts at least to some extent.

Cataracts cannot currently be cured, reversed, or even significantly arrested. Accordingly, the corrective action involves surgically removing the natural lens when the lens becomes so cloudy that vision is greatly impaired, the result being that a phakic eye becomes an aphakic eye.

After a defective natural lens has been surgically removed, the current vision-restoring practice (since about the 1940's) is to implant in the aphakic eye an artificial refractive lens called an intraocular lens (IOL) having an optic and optic fixation means. Previously, thick, heavy, high diopter spectacles were prescribed for aphakic eyes. Such spectacles however were and still are generally disliked by most patients for their weight and appearance.

Implantable IOLs were initially constructed from rigid polymethyl methacrylate (PMMA), a hard, biocompatible plastic material. More recently, IOLs have been constructed from a soft, elastically deformable, silicone or acrylate material that enables insertion of the IOLs through small ocular incisions.

In addition to the implanting of IOLs in aphakic eyes to restore vision after removal of the natural lens, considerable interest has recently arisen in implanting IOLs in phakic eyes to correct myopia, hyperopia, presbyopia or astigmatism problems associated with non-cataract natural lenses. This implanting of corrective IOLs in phakic eyes is an often-attractive alternative to the wearing of corrective spectacles or contact lenses, which limit certain activities and even certain professions, or having performed such surgical procedures on the cornea as radial keratomy (RK) or photoradial keratectomy (PRK), which may not be desired by many individuals for various reasons. The implanting of refractive IOLs in phakic eyes to correct vision problems is considered to constitute one of the remaining frontiers of vision correction.

In an aphakic eye, a replacement IOL is now typically implanted in the posterior chamber of the eye from which the natural lens has been removed. In contrast, a corrective IOL for a phakic eye is most desirably implanted in the anterior chamber of the eye, forwardly of the intact natural lens in the posterior chamber of the eye. The former is called a posterior chamber IOL and the latter is called an anterior chamber IOL, and there are significant construction differences between the two types of IOLs.

With regard to anterior chamber IOLs, there has been renewed interest in IOLs constructed for fixation to the iris (some of the earliest IOLs were iris fixated, anterior chamber IOLs). By fixing the optic supporting structure to the iris itself, contact with the sensitive filtration angle of the eye is avoided.

Iris fixated IOLs are disclosed in U.S. Pat. Nos. 4,215,440 and 5,192,319 to Jan Worst. Both of such patents disclose IOLs employing one or more optic fixation members formed having a pair of pincer arms which, acting together, pinch an anterior surface region of the iris. This pinching action detachably attaches the IOL to the iris so that the IOL optic is ideally fixated in the region of the iris opening (i.e., the pupil of the eye).

However, the present inventor considers that improvements to the iris fixated IOL designs disclosed in the two above-cited Worst patents are desirable and it is a principal objective of the present invention to provide such improvements, particularly in the areas of improving optic centration and enabling small incision implanting.

SUMMARY OF THE INVENTION

In accordance with the present invention, there is provided an iris fixated intraocular lens which comprises an optic having an optical axis and anterior and posterior sides and at least two fixation members, and which may have an overall diameter of between about 7.5 mm and about 10 mm. Each of the fixation members have a proximal end region and a distal end region, the proximal end region comprising a flexible strand, preferably, a single flexible strand, fixed to an edge region of the optic so as to extend generally tangentially outwardly therefrom. The distal end region is formed into a loop having defined therein at least one narrow iris pincher gap.

In a preferred embodiment of the invention, the at least one pincher gap is located on a line generally perpendicular to the optical axis, but may alternatively be formed at an angle to the perpendicular line.

It is preferred that the at least two fixation members include first and second fixation members that are substantially identical to one another and are attached to the optic on opposite sides of the optical axis. The first and second fixation members are constructed separately from the optic, the intraocular lens being thereby a three-piece intraocular lens.

It is further preferred that the optic is constructed from an elastically deformable material, which may be a silicone material or an acrylic material. Also, the at least two fixation members lie in an at least substantially common plane located posterior of the optic.

The distal end loop of each of the at least two fixation members may be elongated into a curved shape, and in some embodiments of the invention, each of the distal end loop includes means dividing the loops into first and second segments; in which case, a first pincer gap is defined in the first loop segment and a second pincer gap is defined in the second loop segment. Preferably, the loop dividing means lies generally perpendicular to the optical axis of the optic.

The at least one pincer gap preferably has a width of between about 0.05 mm and about 0.25 mm, and preferably has a length between about 0.2 mm and about 0.5 mm. The pincer gap in the distal end loop of each of the first and second fixation members may be located in a region of the loop closest to said optical axis, or in a region of the loop furthest from said optical axis. In either case, the pincer gaps are spaced a preferred distance, D, between about 8.0 mm and about 9.0 mm, away from the optical axis of the optic.

Because the fixation members are constructed as a flexible strand and the optic is constructed from an elastically deformable material, the resulting three piece iris fixated IOL of the invention can be folded, rolled or otherwise deformed for insertion through a small, sutureless incision in the eye, as is highly desirable for such reasons as minimal patient trauma and the reduced possibility of surgical complications. Also importantly, the flexible strand fixation members enable accurate centration of the associated optic in the patient's eye upon fixation of the IOL to the iris.

BRIEF DESCRIPTION OF THE DRAWINGS

The present invention can be more readily understood by a consideration of the following detailed description when taken in conjunction with the accompanying drawings, in which:

FIG. 2 is a front view of one embodiment of a three piece iris fixated IOL of the present invention, showing the optic and an opposing pair of optic support or fixation members (haptics), each terminating in an elongated fixation loop having a narrow pincer gap for enabling detachable attachment of the IOL to the anterior surface of a patient's iris, the pincer gaps being shown directly facing the optic;

FIG. 3 is a side view of the IOL of FIG. 2, showing forward vaulting of the optic relative to the fixation loops;

FIG. 4 is a partial front view of a variation fixation loop corresponding to the fixation loops shown in FIG. 2, showing a spaced apart pair of iris pincer gaps defined in the elongated vertically-divided fixation loop, both of such gaps shown directly facing the optic;

In the various FIGS., the same elements and features are given the same reference numbers. In the various variation embodiments, corresponding elements and features are given the same reference numbers as first set forth, followed by an "a", "b", "c", and so on, as appropriate and as will be evident in the following DESCRIPTION.

DESCRIPTION OF THE PREFERRED EMBODIMENT

Figure 1:
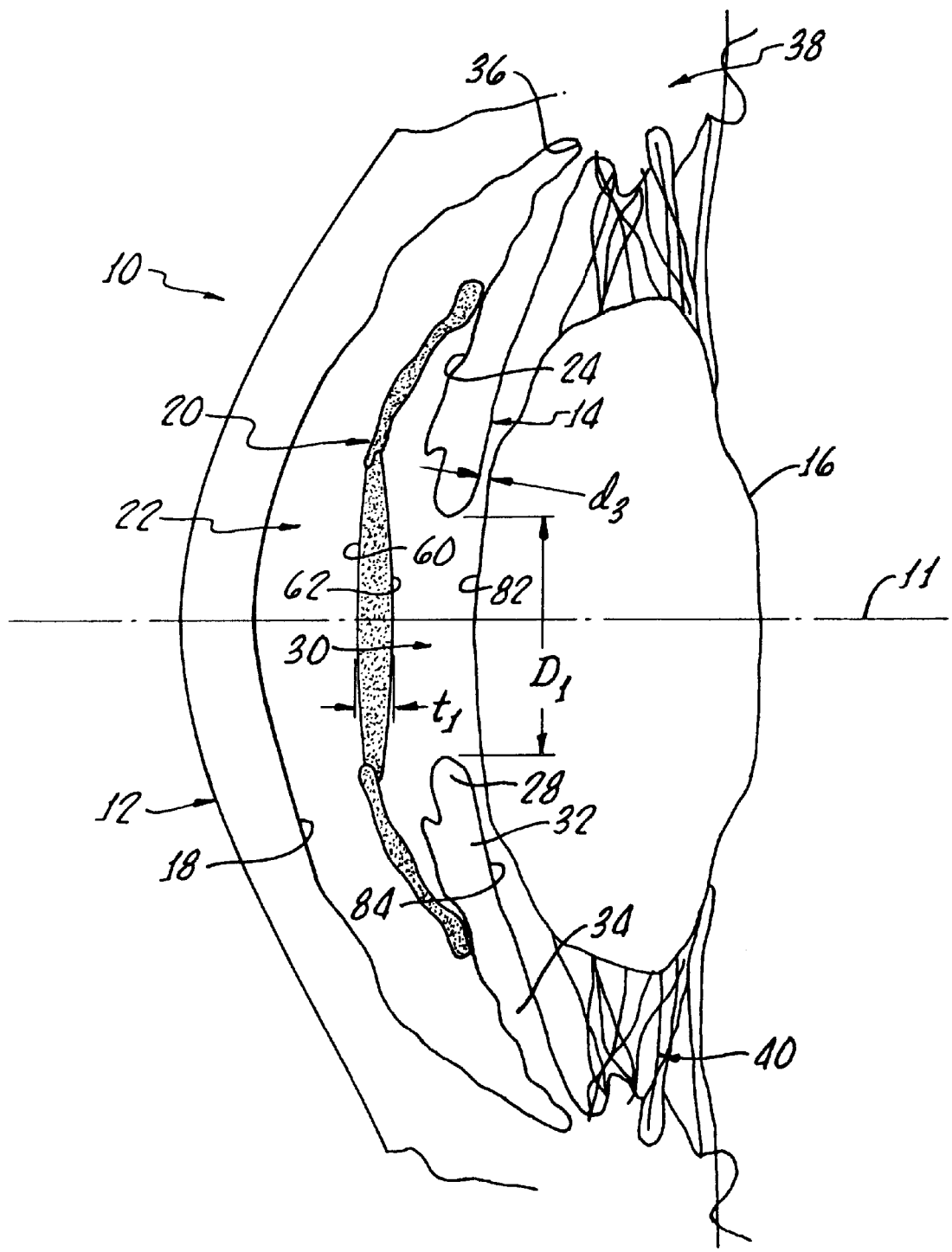
FIG. 1 is a vertical cross sectional drawing of forward regions of a representative human eye, showing the cornea, iris and natural lens and showing an iris fixated intraocular lens (IOL) of the present invention implanted in the anterior chamber of the eye and fixed to the anterior surface of the iris.

There is shown in FIG. 1, in vertical cross section, a forward region 10 of a representative human eye having an optical axis 11 (Axis of symmetry). Depicted in the FIG. are a cornea 12, an iris 14 and an intact, natural crystalline lens 16. A (posterior) corneal endothelium surface 18 is identified on cornea 12.

An iris fixated intraocular lens (IOL) 20, according to a preferred embodiment of the present invention, is shown implanted in an anterior chamber 22 of eye region 10 (posterior to corneal endothelium surface 18) and fixated, in a manner described below, to an anterior surface 24 of iris 14.

Identified in FIG. 1, to facilitate the understanding of the present invention, is an annular pupiliary spincter region 28 of iris 14 that surrounds and controls a pupil or pupiliary opening 30 having a diameter, $D_1$, that typically no greater than about 8 mm for normal vision.

Further identified are an annular iris collarette region 32 and an annular pupiliary dilator muscle region 34 of iris 14. An annular chamber angle 36 is identified at a peripheral edge region of iris 14, as is an annular trabecular meshwork 38. An annular ciliary processes 40 is indicated at the peripheral attachment of natural lens 16.

As is further depicted in FIG. 1, iris fixated IOL 20 is fixated to iris anterior surface 24 in the general region of iris collarette 32 (the thickest region of iris 14), radially outwardly from pupillary sphincter 28.

Shown in FIGS. 2 and 3, comprising iris fixated IOL 20 are an optic 50 and a pair of opposing, similar and preferably identical, fixation members or haptics 52. Projecting sidewardly (radially) from opposite sides of a peripheral edge 56 of optic 50, and preferably formed in one piece with the optic, are similar structural haptic attachment abutments or bosses 58. Optic 50, which has respective anterior and posterior surfaces 60 and 62 (FIGS. 1 and 3), may be constructed as convex-convex (as depicted in FIG. 1), convex-concave, convex-planar, or concave-planar or concave-concave, all such and other configurations being within the scope of the present invention. Optic 50 may advantageously be provided in the diopter range between about −15 and about +15.

It is preferred that optic 50 be constructed from an elastically deformable material, such as a silicone or acrylic material, enabling the optic to be folded, rolled or otherwise deformed so that IOL 20 can be implanted through an ocular incision no larger than about 3.5 mm. It is therefore preferable that the material from which optic 50 is constructed have an index of refraction of at least about 1.46 and that the optic have a diameter, $D_2$, of between about 5.5 mm and about 7.0 mm (FIG. 3) and a center thickness, $t_1$, no greater than about 0.8 mm (FIG. 1).

Each of haptics 52, which are preferably constructed (as by micro-machining) from polymethyl methacrylate (PMMA), is formed having an arcuate, flexible proximal end region 70 and a generally flat, loop-shaped distal end region 72. A proximal end 74 of each haptic 52 is fixed into an associated one of bosses 58 (FIG. 2) so that haptic proximal end region 70 extends in a direction tangential to optic edge 56. Such haptic-to-optic fixation can be of any type used by IOL manufacturers for the secure attachment of haptics to soft, flexible optics.

Haptic proximal end region 70 is arcuate in plan view and arches away from optic 50 (FIG. 2). Further, proximal end region 70 is made flexible, particularly in a plane parallel to the plane of optic 50, by preferably having a width, $w_1$, of about 0.25 mm and a thickness, $t_2$ (FIG. 3) of about 0.35 mm. Preferably portions of haptic 52 defining distal end region loop 72 have about the same thickness as set forth for haptic proximal end region 70, and may be somewhat wider, as set forth below.

The loop into which haptic distal end region 72 is formed may be of a variety of shapes. However, the end region loop is shown in FIG. 2 as being elongated into a curved shape having a length, $l_1$ and flattened into a width, $w_2$. By way of example, with no limitation intended or implied, such loop length, $l_1$, may be about 3.0 mm and such loop width, $w_2$, may be about 1.0 mm.

A side region 76 of distal end region loop 72 that is closest to and directly faces optic 50 is formed defining an iris pincer gap 78 (FIG. 2) having a width, $w_3$, of about 0.1 mm and a length, $l_2$, of about 0.4 mm. Iris pincer gap 78 is shown oriented in a radial direction relative to a center 80 of optic 50, but may alternatively be oriented in another direction. As further, shown in FIG. 2, both iris pincer gaps 78 of the two haptics 52 are centered on a diameter, $D_3$, which is preferably about 8.5 mm. Pincer gaps 78 of both haptics 52 also lie generally on a common plane 82 (FIG. 3), the haptics being arched so that optic 50 is vaulted forwardly into anterior chamber 22 (FIG. 1) with posterior surface 62 anterior of plane 82 by a distance, $d_1$, that is preferably about 0.5 mm.

Overall diameter, $D_4$ of IOL 20 (to ends of haptics 52) is preferably between about 7.5 mm and about 10 mm so that the IOL haptics engage iris 14 at iris collarette region 32, as noted above (FIG. 1).

As a result of the flexibility of haptics 52, after one haptic has been attached to iris 14 by a pinching action (more particularly described below), optic center 80 can be easily aligned with optical axis 11 by flexing of the second haptic 52 before the second haptic is attached to the iris. Thus, centration of optic 50 on optical axis 11 of the eye is easily achieved.

Moreover, with optic 50 constructed from an elastically deformable material, IOL 20 can be implanted through a small ocular incision, as is important to minimize surgical trauma and possible complications, and reduce patient recovery time, all as compared to the surgical procedure required to implant a rigid iris fixation IOL. Further in this regard, the explanting of the flexible IOL 20, in the event explanting becomes necessary as the patient's vision changes with time, is also made easier.

From the foregoing, it will be appreciated that many variations to IOL 20 and particularly to haptics 52 which attach the IOL to iris 14 are possible and are to be considered as being covered by the present invention.

IOL VARIATION OF FIG. 4

One of such variations is shown in FIG. 4 in connection with a variation IOL 20a, which is identical for descriptive purposes to above-described IOL 20 except as otherwise particularly described below. Corresponding elements and features are given the same reference numbers set forth above followed by an "a".

As shown, a looped distal end region 72a of a haptic 52a (corresponding to haptic 52) is divided radially (relative to center 80 of optic 50) by a narrow wall 90 into respective first and second loop sectors 92 and 94. Each such sector 92 and 94 is constructed to define an iris pincer gap 78 directly facing optic 50. Thus, each haptic 52a (only a representative one of which is shown) incorporates in distal end region 72a a spaced-apart pair of iris pincer gaps 78. This described doubling of the number of iris pincer gaps 78 in haptic loops 72a may sometimes be advantageous in securely detachably fixing IOL 20a to iris 14.

IOL VARIATION OF FIGS. 5 AND 6

Figure 5:
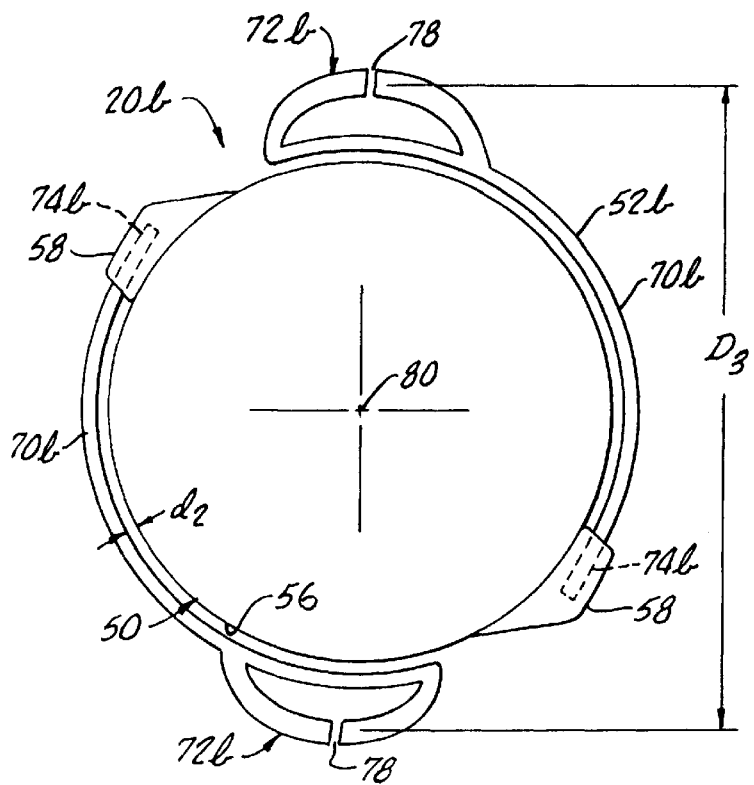
FIG. 5 is a front view of a variation three piece iris fixated IOL of the present invention, showing the optic and an opposing pair of haptics, each such haptic shown curving closely around the optic and terminating in an elongated fixation loop having a narrow, perpendicular pincer gap for enabling detachable attachment of the IOL to a patient's iris, the pincer gaps being shown facing away from the optic.
Figure 6:
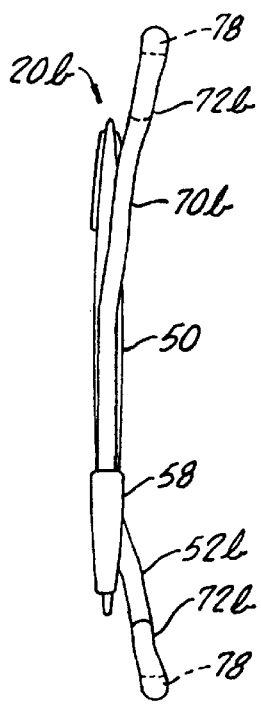
FIG. 6 is a side view of the IOL of FIG. 5, showing forward vaulting of the optic relative to the fixation loops.

Another such variation is shown in FIGS. 5 and 6 in connection with a variation iris fixation IOL 20b, which is identical for descriptive purposes to above-described IOL 20 except as otherwise particularly described below. Corresponding elements and features are given the same reference numbers set forth above followed by a "b".

A principal distinction between IOL 20b and above-described IOL 20 relates to pincer gaps 78 on haptic loops 72b facing away from optic 50 instead of directly facing the optic in the case of above-described IOL 20. Because pincer gaps 78 are spaced apart the same distance, $D_3$ (before disclosed in connection with IOL 20), proximal regions 70b of haptics 52b curve more closely around optic 50. Haptics 52b, are generally spaced from optic edge 56 a distance, $d_2$, that is at least about equal to a closest separation distance, $d_3$ (FIG. 1), between anterior surface 82 of natural lens 16 and posterior surface 84 of iris 14 (a distance typically of about 0.3 mm).

Since haptics 52b are otherwise similar to above-described haptics 52, this increased, C-curvature of haptics 52b may provide somewhat increased haptic flexibility. Moreover, orienting pincer gaps 78 on haptic loops 72b away from optic 50 may, in some instances, facilitate fixation of the IOL to iris 14. The vaulting of optic 50 relative to haptic loops 72b is preferably the same as disclosed above relative to IOL 20.

IOL VARIATION OF FIG. 7

Figure 7:
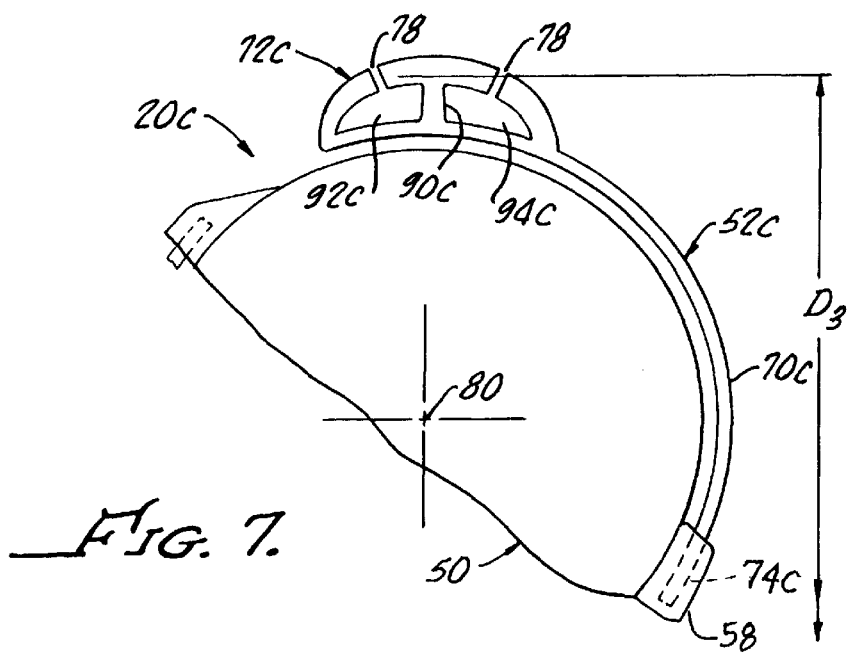
FIG. 7 is a partial front view of a variation fixation loop corresponding to the fixation loops shown in FIG. 5, showing a spaced apart pair of iris pincer gaps defined in the elongated vertically-divided fixation loop, both of such gaps shown directed away from the optic.

FIG. 7 depicts another variation iris fixated IOL 20c, which is identical for descriptive purposes to above-described IOL 20b except as otherwise particularly described below. Previously described features and elements are given the same reference number followed by a "c".

As can be seen, IOL 20c combines the described double pincer gap features shown for IOL 20a in FIG. 4 with IOL 20b (FIGS. 5 and 6.). Thus, as shown in FIG. 7, representative haptic loop 72c is vertically divided by a narrow wall 90c into first and second loop sectors 92c and 94c, respectively. Each sector 92c and 94c has defined a pincer gap 78 that faces away from associated optic 50.

Pincer gaps 78 on both haptic loops 72c (only one such loop being shown) are spaced a distance $D_3$ (defined above) apart.

OPERATION OF PINCER GAPS

Figure 8:
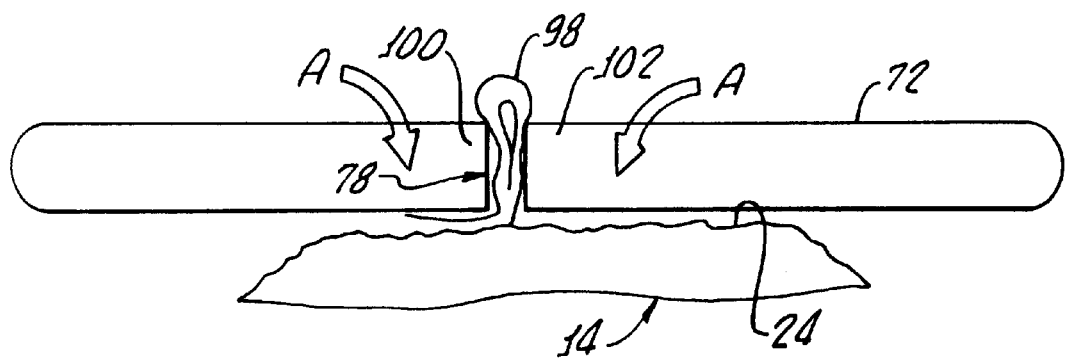
FIG. 8 is a drawing depicting the manner in which a representative right angle pincer gap, such as those shown in FIGS. 2, 4, 5 and 7, is operative for pinching an anterior surface region of an iris in a manner detachably attaching the associated fixation loop and thus the associated IOL to the iris.

FIG. 8 depicts the manner in which a representative one of pincer gaps 78, on a representative haptic distal end region loop 72 pinches up a small surface segment 98 of iris tissue into the gap, thereby releasably or detachably fixing the associated haptic (e.g., haptic 52), and hence the associated IOL (e.g., IOL 20), to iris 14.

This pinching up of iris segment 98 is accomplished, for example, by deflecting haptic loop regions 100 and 102 on each side of gap 78, downwardly (direction of Arrows rows "A") into iris surface 24. When the loop regions are released, they return to their original shape, thereby trapping iris segment 98 in gap 78.

VARIATION IRIS PINCER GAP OF FIG. 9

It is to be understood that variations of the iris pincer gap may be made within the scope of the present invention and used in place of above-described pincer gap(s) 78. An example of such a variation is depicted in FIG. 9, in which a slanted iris pincer gap 78d (corresponding to above-described pincer gap 78) is depicted formed or defined in a representative haptic distal end region loop 72d (corresponding to above-described distal end region loop 72).

Figure 9:
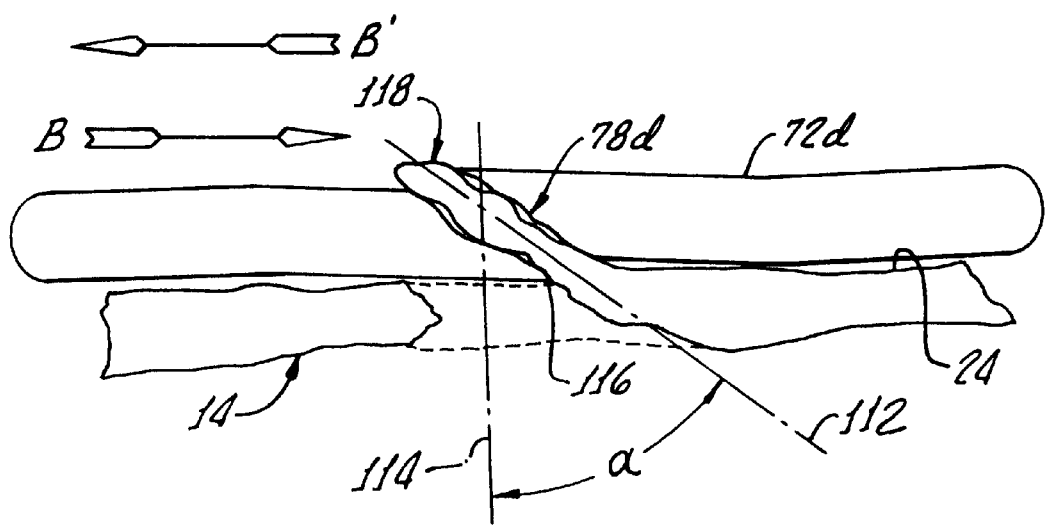
FIG. 9 is a drawing depicting the manner in which a representative angled pincer gap, corresponding to the right angle pincer gaps shown in FIGS. 2, 4, 5 and 7 is used to engage the anterior surface of an iris in a manner detachably attaching the associated fixation loop and thus the associated IOL to the iris.

Pincer gap 78d is depicted in FIG. 9 as formed or defined along a line 112 that is at an angle, α, relative to a line 114 perpendicular to end region loop 72d. Preferably, slant angle, α, is between about 30 degrees and about 60 degrees, with a slant angle of about 45 degrees being most preferred.

It is evident from FIG. 9 that when end region loop 72d is pressed against iris anterior surface 24 and is pushed or advanced in the direction indicated by Arrow "B", a sharp, leading lower edge 116 at gap 78d cuts into iris 14. This causes a small sliver 118 of iris 14 to be extruded into gap 78d, to thereby detachably fixate end region loop 72d, and hence associated haptic and IOL (neither shown in FIG. 9) to iris 14.

Distal end region loop 72d can be detached from iris by merely rotating the end region loop back in the direction indicated by Arrow "B'".

Although there have been described above an iris fixated IOL, and variations thereof, in accordance with the present invention for purposes of illustrating the manner in which the present invention maybe used to advantage, it is to be understood that the invention is not limited thereto. Consequently, any and all variations and equivalent arrangements which may occur to those skilled in the applicable art are to be considered to be within the scope and spirit of the invention as set forth in the claims which are appended hereto as part of this application.

What is claimed is:

1. An iris fixated intraocular lens which comprises:
   a. an optic having an optical axis and anterior and posterior sides; and
   b. at least two fixation members, each of said fixation members having a proximal end region and a distal end region, said proximal end region comprising a flexible strand fixed to an edge region of said optic so as to extend generally tangentially outwardly therefrom, and said distal end region being formed into a loop having defined therein at least one narrow iris pincer gap having a substantially uniform width and being sized for pinching a small surface segment of iris tissue into said gap for detachably attaching said intraocular lens to an iris anterior surface.

2. The iris fixated intraocular lens as claimed in claim 1, wherein said at least one pincer gap being located on a line generally perpendicular to said optical axis and being positioned at a radius from said optical axis of about 4.25 mm.

3. The iris fixated intraocular lens as claimed in claim 1, wherein said at least two fixation members include first and second fixation members, said first and second fixation members being substantially identical to one another and being attached to said optic on opposite sides of said optical axis.

4. The iris fixated intraocular lens as claimed in claim 3, wherein said first and second fixation members are constructed separately from said optic, said intraocular lens being thereby a three-piece intraocular lens.

5. The iris fixated intraocular lens as claimed in claim 4, wherein said optic is constructed from an elastically deformable material.

6. The iris fixated intraocular lens as claimed in claim 5, wherein said elastically deformable material is a silicone material.

7. The iris fixated intraocular lens as claimed in claim 5, wherein said elastically deformable material is an acrylic material.

8. The iris fixated intraocular lens as claimed in claim 1, wherein the distal end loop of each of said at least two fixation members lie in an at least substantially common plane located posteriorally of said optic.

9. The iris fixated intraocular lens as claimed in claim 1, wherein said distal end loop of each of said at least two fixation members is elongated into a curved shape.

10. An iris fixated intraocular lens which comprises:
    a. an optic having an optical axis and anterior and posterior sides;
    b. at least two fixation members, each of said fixation members having a proximal end region and a distal end region, said proximal end region comprising a flexible strand fixed to an edge region of said optic so as to extend generally tangentially outwardly therefrom, and said distal end region being formed into a loop having defined therein at least one narrow iris pincer gap, the distal end loop of each of said at least two fixation members being elongated into a curved shape, each said distal end loop including means dividing said loop into first and second segments.

11. The iris fixated intraocular lens as claimed in claim 10, wherein said dividing means lies generally perpendicular to said optical axis of said optic.

12. The iris fixated intraocular lens as claimed in claim 10, including a first pincer gap defined in said first loop segment and a second pincer gap defined in said second loop segment.

13. The iris fixated intraocular lens as claimed in claim 2, wherein said pincer gap is defined at an angle to said perpendicular line.

14. The iris fixated intraocular lens as claimed in claim 1, wherein said at least one pincer gap has a width of between about 0.05 mm and about 0.25 mm.

15. The iris fixated intraocular lens as claimed in claim 1, wherein said pincer gap has a length of between about 0.2 mm and about 0.5 mm.

16. The iris fixated intraocular lens as claimed in claim 1, wherein the intraocular lens has an overall diameter of between about 7.5 mm and about 10 mm.

17. An iris fixated intraocular lens which comprises:
    a. an optic having an optical axis and anterior and posterior sides; and
    b. first and second fixation members, each of said fixation members having a proximal end region and a distal end region, said proximal end region comprising a single flexible strand fixed to an edge region of said optic so as to extend generally tangentially outwardly therefrom, and said distal end region being formed into a loop having defined therein a narrow iris pincer gap having a substantially uniform width and being located on a line generally perpendicular to said optical axis, said gap being sized for pinching a small surface segment of iris tissue into said gap for detachably attaching said intraocular lens to an iris anterior surface.

18. The iris fixated intraocular lens as claimed in claim 17, wherein said first and second fixation members are substantially identical to one another and are attached to said optic on opposite sides of said optical axis.

19. The iris fixated intraocular lens as claimed in claim 17, wherein the distal end loop of each of said first and second fixation members lie in a generally common plane, and wherein said pincer gaps are located on a diameter, D, through the optical axis of said optic.

20. The iris fixated intraocular lens as claimed in claim 19, wherein said distance, D, is between about 8.0 mm and about 9.0 mm.

21. The iris fixated intraocular lens as claimed in claim 17, wherein said distal end loop of each of said first and second fixation members is elongated into a curved shape having a major axis generally parallel to said optical axis.

22. The iris fixated intraocular lens as claimed in claim 17, wherein the pincer gap in the distal end loop of each of said first and second fixation members is located in a region of said loop closest to said optical axis.

23. An iris fixated intraocular lens which comprises:
   a. an optic having an optical axis and anterior and posterior sides; and
   b. first and second fixation members, each of said fixation members having a proximal end region and a distal end region, said proximal end region comprising a single flexible strand fixed to an edge region of said optic so as to extend generally tangentially outwardly therefrom, and said distal end region being formed into a loop having defined therein a narrow iris pincher gap located on a line generally perpendicular to said optical axis, the pincer gap in the distal end loop of each of said first and second fixation members being located in a region of said loop furthest from said optical axis.

24. An iris fixated intraocular lens which comprises:
   a. an optic having an optical axis and anterior and posterior sides; and
   b. first and second fixation members, each of said fixation members having a proximal end region and a distal end region, said proximal end region comprising a single flexible strand fixed to an edge region of said optic so as to extend generally tangentially outwardly therefrom, and said distal end region being formed into a loop having defined therein a narrow iris pincher gap located on a line generally perpendicular to said optical axis, each of said distal end loops including means dividing the loop into first and second loop segments, said dividing means lying along a line generally perpendicular to said optical axis, and including a first pincer gap defined in said first loop segment and a second pincer gap defined in said second loop segment.

25. The iris fixated intraocular lens as claimed in claim 17, wherein said pincer gap has a width of between about 0.05 mm and about 0.25 mm and a length of between about 0.2 mm and about 0.5 mm.

26. A three-piece iris fixated intraocular lens which comprises:
   a. an optic having an optical axis and anterior and posterior sides, said optic being constructed from an elastically deformable plastic material; and
   b. first and second fixation members, each of said fixation members having a proximal end region and a distal end region, said proximal end region comprising a single flexible strand attached to an edge region of said optic so as to extend generally tangentially outwardly therefrom, and said distal end region being formed into a loop having defined therein at least one narrow iris pincher gap having a substantially uniform width and being sized for pinching a small surface segment of iris tissue into said gap for detachably attaching said intraocular lens to an iris anterior surface.

27. The three-piece iris fixated intraocular lens as claimed in claim 26, wherein said first and second fixation members are substantially identical to one another and are attached to said optic on opposite sides of said optical axis.

28. The three-piece iris fixated intraocular lens as claimed in claim 26, wherein said at least one pincer gap in the distal end loop of each of said first and second fixation members is located in a region of said loop closest to said optical axis.

29. A three-piece iris fixated intraocular lens which comprises:
   a. an optic having an optical axis and anterior and posterior sides, said optic being constructed from an elastically deformable plastic material; and
   c. first and second fixation members, each of said fixation members having a proximal end region and a distal end region, said proximal end region comprising a single flexible strand attached to an edge region of said optic so as to extend generally tangentially outwardly therefrom, and said distal end region being formed into a loop having defined therein at least one narrow iris pincher, said at least one pincer gap in the distal end loop of each of said first and second fixation members being located in a region of said loop furthest from said optical axis.

* * * * *